(12) United States Patent
O'Dea

(10) Patent No.: US 8,827,929 B2
(45) Date of Patent: Sep. 9, 2014

(54) METHOD AND APPARATUS FOR DETERMINING THE DISTENSIBILITY OF A VESSEL, LUMEN OR A SPHINCTER

(75) Inventor: John O'Dea, Bearna (IE)

(73) Assignee: Flip Technologies Limited, Dangan (IL)

( * ) Notice: Subject to any disclaimer, the term of this patent is extended or adjusted under 35 U.S.C. 154(b) by 496 days.

(21) Appl. No.: 12/788,539

(22) Filed: May 27, 2010

(65) Prior Publication Data

US 2010/0305479 A1 Dec. 2, 2010

(30) Foreign Application Priority Data

May 28, 2009 (IE) .................................. S2009/0419

(51) Int. Cl.
*A61B 5/103* (2006.01)
*A61B 5/117* (2006.01)

(52) U.S. Cl.
USPC ........... 600/587; 600/485; 600/486; 600/487; 600/591; 600/593

(58) Field of Classification Search
USPC .......... 600/485–489, 505, 507, 587, 591, 593
See application file for complete search history.

(56) References Cited

U.S. PATENT DOCUMENTS

| | | | |
|---|---|---|---|
| 5,275,169 A * | 1/1994 | Afromowitz et al. ......... | 600/486 |
| 2004/0215235 A1* | 10/2004 | Jackson et al. .................... | 607/2 |
| 2007/0083126 A1* | 4/2007 | Marko et al. ................... | 600/505 |
| 2008/0027358 A1* | 1/2008 | Gregersen et al. ............ | 600/593 |
| 2008/0161730 A1* | 7/2008 | McMahon et al. ............ | 600/593 |

OTHER PUBLICATIONS

Dall et al. (article entitled "Biomechanical Wall Properties of the human rectum: A study with impedance planimetry," Gut 1993; 34:1581-1586).*
Gerda et al., article entitled "Impedance Planimetric Characterization of Esophagus in Systemic Sclerosis Patients with Severe Involvement of Esophagus," Digestive Diseases and Sciences, vol. 42, No. 11 (Nov. 1997), pp. 2317-2326.*

* cited by examiner

Primary Examiner — Rene Towa
(74) Attorney, Agent, or Firm — Sughrue Mion, PLLC

(57) ABSTRACT

An apparatus for measuring distensibility of a vessel, lumen or sphincter includes a balloon catheter having a balloon located adjacent a distal end of a catheter for inserting in, for example, the sphincter, the distensibility of which is to be determined. The balloon is inflated to respective first and second pressures to distend the sphincter to respective first and second transverse cross-sectional areas which are measured. The first and second pressures are selected so that the relationship between the pressure and the cross-sectional area of the sphincter is linear. The distensibility of the sphincter is determined as a distensibility index, which is the value of c from the equation of a line y=mx+c containing the values of the first and second pressures and areas, where x represents pressure and y represents area.

10 Claims, 7 Drawing Sheets

Figure 1:
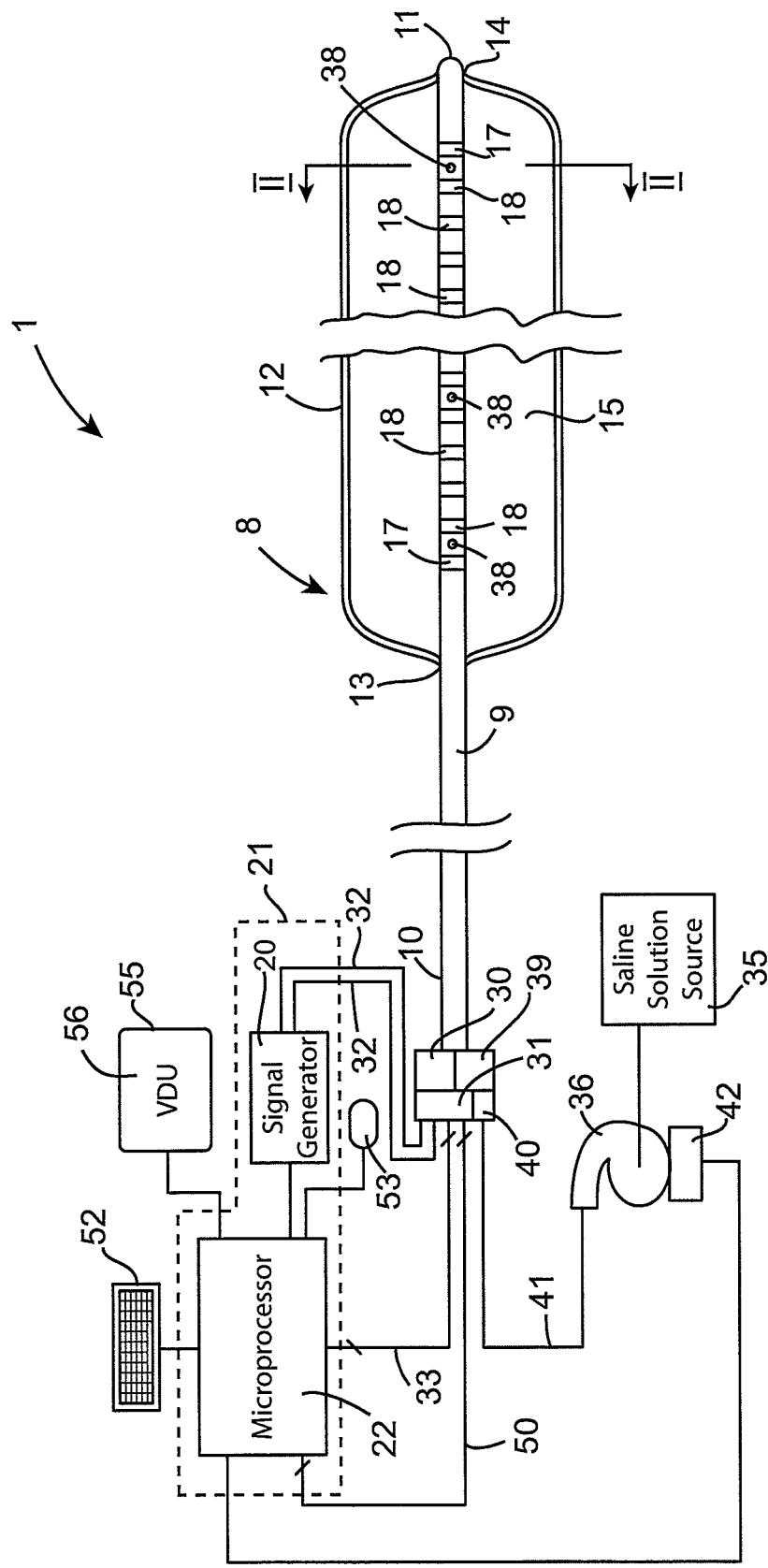

METHOD AND APPARATUS FOR DETERMINING THE DISTENSIBILITY OF A VESSEL, LUMEN OR A SPHINCTER

The present invention relates to a method and apparatus for determining the distensiblility of a sphincter, and the invention also relates to a method and apparatus for determining the distensibility of a vessel or a lumen, and in particular, for determining the distensibility of a wall of a vessel or a lumen. The invention also relates to a method and apparatus for determining a distensibility index of a vessel, a lumen or sphincter.

The tone of the walls of vessels and lumens in the human and animal body tends to deteriorate as the human or animal ages. This deterioration tends to be as a result of thinning or weakening of the wall of the vessel or lumen, and where the wall of such vessels or lumens is supported by a muscle group, deterioration in the tone of the vessel or lumen wall tends to result from a deterioration in the tone of the muscle group. Indeed, in the cardiovascular system, deterioration of the tone of the wall of a vessel or a lumen may result from a build-up of plaque on the inner surface of the wall of the vessel or lumen. In order to detect the onset of certain diseases and undesirable conditions in the human or animal body, it is necessary to determine the extent to which the tone of the wall of certain vessels and lumens has deteriorated, and in particular, the extent to which the tone of a muscle group which is supporting the wall of the vessel or lumen has deteriorated. Unfortunately, there is no satisfactory method or apparatus for determining the tone or the extent of deterioration of the tone of the wall of such vessels and lumens or the corresponding muscle group.

The tone of muscle groups which extend around sphincters in the human and animal body also tend to deteriorate with aging. This deterioration of the tone of such muscle groups results in the corresponding sphincter being more easily distensible, and ultimately may lead to failure of the sphincter to close. Again, it is important to detect the extent of deterioration in the tone of muscle groups of such sphincters in order to detect the onset of diseases and undesirable conditions of the human and animal body. For example, a condition known as gastro-oesophageal reflux disease (GERD) results from a deterioration of the muscle group associated with the lower oesophageal sphincter. In order to detect the onset of GERD, and indeed, to determine the seriousness of GERD in a subject, it is necessary to determine the tone of the muscle group associated with the lower oesophageal sphincter. There is no satisfactory method or apparatus for determining the tone of the muscle group associated with the lower oesophageal sphincter, nor is there any satisfactory method or apparatus for determining the seriousness of GERD in a subject.

There is therefore a need for a method and apparatus for determining the tone of a wall of a vessel or lumen and for determining the tone of a sphincter, and in particular, for determining the tone of a muscle group associated with a sphincter, or associated with a wall of a vessel or lumen.

The present invention is directed towards providing a method and apparatus for determining the distensibility of a wall of a vessel or a lumen and for determining the distensibility of a sphincter, and the invention is also directed towards a method and apparatus for determining the distensibility of a muscle group associated with a vessel, lumen or sphincter. The invention is also directed towards providing a method and apparatus for determining a distensibility index of a vessel, a lumen or a sphincter.

According to the invention there is provided apparatus for determining the distensibility of one of a vessel wall, a lumen wall and a sphincter, the apparatus comprising:
- a balloon catheter comprising an elongated catheter extending between a proximal end and a distal end, and an inflatable element defining a hollow interior region when inflated located on the catheter, the inflatable element being adapted for locating in the one of the vessel, the lumen and the sphincter,
- a communicating means for communicating the hollow interior region of the inflatable element with an inflating means for inflating the inflatable element with an inflating medium,
- a pressure sensing means for monitoring the pressure of the inflating medium in the inflatable element,
- a measuring means for measuring the transverse cross-sectional area of the inflatable element, and
- a computing means adapted to determine the distensibility of the one of the vessel wall, the lumen wall and the sphincter as a function of one of the transverse cross-sectional area of the inflatable element adjacent the portion of the one of the vessel wall, the lumen wall and the sphincter, at which the distensibility is to be determined and the corresponding pressure of the inflating medium in the inflatable element when the inflatable element is inflated to one of a pressure and a transverse cross-sectional area sufficient to distend the one of the vessel wall, the lumen wall and the sphincter.

In one embodiment of the invention the computing means is adapted to determine the distensibility of the one of the vessel wall, the lumen wall and the sphincter as a function of the ratio of the transverse cross-sectional area of the inflatable element adjacent the portion of the one of the vessel wall, the lumen wall and the sphincter, at which the distensibility is to be determined to the corresponding pressure of the inflating medium in the inflatable element.

In another embodiment of the invention the computing means is adapted to determine the distensibility of the one of the vessel wall, the lumen wall and the sphincter as a function of the one of the transverse cross-sectional area of the inflatable element adjacent the portion of the one of the vessel wall, the lumen wall and the sphincter, at which the distensibility is to be determined and the pressure of the inflating medium in the inflatable element when the inflatable element is inflated to one of a first pressure and a first transverse cross-sectional area.

Preferably, the computing means is adapted to determine the distensibility of the one of the vessel wall, the lumen wall and the sphincter as the value of the transverse cross-sectional area of the inflatable element adjacent the portion of the one of the vessel wall, the lumen wall and the sphincter at which the distensibility is to be determined when the inflatable element is inflated to the first pressure.

Advantageously, the computing means is responsive to the inflatable element being inflated to the one of the first pressure and the first transverse cross-sectional area adjacent the portion of the one of the vessel wall, the lumen wall and the sphincter, at which the distensibility is to be determined, for determining the distensibility of the one of the vessel wall, the lumen wall and the sphincter.

In another embodiment of the invention the computing means is adapted to determine the distensibility of the one of the vessel wall, the lumen wall and the sphincter, as a function of two values of the transverse cross-sectional area of the inflatable element adjacent the portion of the one of the vessel wall, the lumen wall and the sphincter at which the distensibility is to be determined and two values of the pressure of the inflating medium in the inflatable element corresponding to the two values of the transverse cross-sectional area thereof.

In another embodiment of the invention the computing means is adapted to determine the distensibility of the one of the vessel wall, the lumen wall and the sphincter as a function of the ratio of the difference between the two values of the transverse cross-sectional area of the inflatable element adjacent the portion of the one of the vessel wall, the lumen wall and the sphincter, at which the distensibility is to be determined to the difference between the two corresponding values of the pressure of the inflating medium in the inflatable element.

In another embodiment of the invention the computing means is adapted to determine the distensibility of the one of the vessel wall, the lumen wall and the sphincter, as a function of an equation of a line containing two values of the transverse cross-sectional area of the inflatable element adjacent the portion of the one of the vessel wall, the lumen wall and the sphincter at which the distensibility is to be determined and two values of the pressure of the inflating medium in the inflatable element corresponding to the two values of the transverse cross-sectional area thereof, the line being a plot of the transverse cross-sectional area of the inflatable element adjacent the portion of the one of the vessel wall, the lumen wall and the sphincter, at which the distensibility is to be determined against the corresponding pressure of the inflating medium in the inflatable element.

Preferably, the computing means is adapted to determine the distensibility of the one of the vessel wall, the lumen wall and the sphincter in the form of a distensibility index, the distensibility index being a function of the value of a point of intersection of the axis on which one of the transverse cross-sectional area and the pressure is plotted by the line containing the two values of the transverse cross-sectional area of the inflatable element and the corresponding pressures of the inflating medium in the inflatable element.

Advantageously, the computing means is adapted to determine the distensibility index of the one of the vessel wall, the lumen wall and the sphincter as a function of the value of the point of intersection of the axis on which the transverse cross-sectional area of the inflatable element is plotted by the line containing the two values of the transverse cross-sectional area of the inflatable element and the corresponding pressures of the inflating medium in the inflatable element.

Ideally, the computing means is adapted to determine the distensibility of the one of the vessel wall, the lumen wall and the sphincter as a function of the equation of the line containing the two values of the transverse cross-sectional area of the inflatable element adjacent the portion of the one of the vessel wall, the lumen wall and the sphincter at which the distensibility is to be determined and the two corresponding values of the pressure of the inflating medium in the inflatable element when the inflatable element is inflated to the one of a first pressure and a second pressure and a first transverse cross-sectional area and a second transverse cross-sectional area adjacent the portion of the one of the vessel wall, the lumen wall and the sphincter, at which the distensibility is to be determined.

In one embodiment of the invention the computing means is responsive to the inflatable element being inflated to one of the first pressure and the second pressure and the first transverse cross-sectional area and a second transverse cross-sectional area adjacent the portion of the one of the vessel wall, the lumen wall and the sphincter, at which the distensibility is to be determined for determining the distensibility of the one of the vessel wall, the lumen wall and the sphincter.

In another embodiment of the invention the inflatable element is inflated to the one of the first pressure and the first transverse cross-sectional area prior to being inflated to the one of the second pressure and the second transverse cross-sectional area, the first pressure and the first transverse cross-sectional area being less than the second pressure and the second transverse cross-sectional area, respectively, and the computing means is responsive to the inflatable element being inflated to the one of the second pressure and the second transverse cross-sectional area for determining the distensibility of the one of the vessel wall, the lumen wall and the sphincter.

In one embodiment of the invention the value of the one of the pressure of the inflating medium in the inflatable element and the transverse cross-sectional area of the inflatable element adjacent the portion of the one of the vessel wall, the lumen wall and the sphincter, at which the distensibility is to be determined is a value at which the relationship between the transverse cross-sectional area of the inflatable element adjacent the portion of the one of the vessel wall, the lumen wall and the sphincter, at which the distensibility is to be determined and the pressure of the inflating medium in the inflatable element is a linear relationship.

In an alternative embodiment of the invention the computing means is adapted for determining the distensibility of the one of the vessel wall, the lumen wall and the sphincter as a function of one of the transverse cross-sectional area of the inflatable element adjacent the portion of the one of the vessel wall, the lumen wall and the sphincter at which the distensibility is to be determined and the corresponding pressure of the inflating medium in the inflatable element at a point at which the relationship between the transverse cross-sectional area of the inflatable element adjacent the portion of the one of the vessel wall, the lumen wall and the sphincter, at which the distensibility is to be determined and the pressure of the inflating medium in the inflatable element transitions from being a substantially linear relationship to a substantially non-linear relationship.

In one embodiment of the invention the apparatus is adapted for determining the distensibility of a sphincter, and the inflatable element comprises an elongated inflatable element extending between a proximal end and a distal end, and being adapted for locating in the sphincter with the sphincter located intermediate the proximal end and the distal end thereof, so that when inflated, the sphincter shapes the inflatable element to define a portion of minimum transverse cross-sectional area adjacent the sphincter, and the computing means is adapted for determining the distensibility of the sphincter as a function of the value of the transverse cross-sectional area of the inflatable element adjacent the portion of minimum transverse cross-sectional area and the corresponding pressure of the inflating medium in the inflatable element when the inflatable element is inflated to a pressure sufficient to distend the one of the vessel wall, the lumen wall and the sphincter.

In another embodiment of the invention the computing means is responsive to the pressure sensing means detecting the inflatable element having been inflated to the first and second pressures for determining the distensibility of the one of the vessel wall, lumen wall and the sphincter.

Ideally, the computing means is adapted for detecting the portion of the inflatable element of the minimum transverse cross-sectional area, and preferably, the value of each transverse cross-sectional area of the inflatable element of the function by which the distensibility of the one of the vessel wall, the lumen wall and the sphincter is determined is the value of the minimum transverse cross-sectional area of the inflatable element when the inflatable element is inflated to the corresponding one of the first pressure and the first transverse cross-sectional area and the one of the second pressure and the second transverse cross-sectional area.

In one embodiment of the invention the measuring means comprises at least one stimulating electrode located on one of the catheter and the inflatable element within the hollow interior region of the inflatable element for receiving a stimulating signal, and at least one sensing electrode located on one of the catheter and the inflatable element within the hollow interior region of the inflatable element and axially spaced apart from the at least one stimulating electrode for producing a response signal indicative of the transverse cross-sectional area of the inflatable element adjacent the corresponding sensing electrode in response to the stimulating signal applied to the at least one stimulating electrode when the inflatable element is inflated with an electrically conductive inflating medium.

In another embodiment of the invention a pair of axially spaced apart stimulating electrodes are provided, and a plurality of axially spaced apart sensing electrodes are provided between the stimulating electrodes and axially spaced apart therefrom.

Preferably, the stimulating and sensing electrodes are located on the catheter.

In one embodiment of the invention a signal generator operable under the control of a control means is provided for applying the stimulating signal to the at least one stimulating electrode.

In another embodiment of the invention the computing means comprises a signal processing means for processing the response signal produced on the at least one sensing electrode for determining the transverse cross-sectional area of the inflatable element adjacent the corresponding sensing electrode.

Preferably, the signal processing means is responsive to a signal from the pressure sensing means for determining when the inflatable element has been inflated to the respective first and second pressures.

Ideally, the signal processing means is adapted for determining the minimum transverse cross-sectional area of the inflatable element, and preferably, the signal processing means is adapted for determining the distensibility of the one of the vessel, lumen and sphincter by determining the ratio of the minimum transverse cross-sectional area of the inflatable element to the first pressure when the inflatable element is inflated to the first pressure.

In another embodiment of the invention a wire accommodating lumen extends along the catheter from the proximal end thereof to the inflatable element for accommodating mutually insulated electrically conductive wires from the stimulating and sensing electrodes and the pressure sensing means to the proximal end of the catheter.

In another embodiment of the invention the pressure sensing means is located in the wire accommodating lumen.

In a further embodiment of the invention the pressure sensing means is located within the hollow interior region defined by the inflatable element.

In a still further embodiment of the invention the communicating means comprises an inflating medium accommodating lumen extending through the catheter from the proximal end thereof to the inflatable element for accommodating inflating medium to and from the hollow interior region defined by the inflatable element.

Preferably, the pressure sensing means is located in a protective housing.

Advantageously, the pressure sensing means comprises a pressure sensor.

Preferably, the catheter extends through the inflatable element and defines with the inflatable element an annular hollow interior region.

Advantageously, the inflatable element is located towards the distal end of the catheter.

In one embodiment of the invention the apparatus is adapted for determining the distensibility of one of a biological vessel, a biological lumen and a biological sphincter.

In another embodiment of the invention the apparatus is adapted for determining the distensibility of a sphincter. Advantageously, the signal processing means is adapted for determining the location of the sphincter relative to the inflatable element by determining the location at which the transverse cross-sectional area of the inflatable element is a minimum as being the location of the sphincter on the inflatable element.

In a further embodiment of the invention the apparatus is adapted for determining the distensibility of a lower oesophageal sphincter.

The invention also provides a method for determining the distensibility of one of a vessel wall, a lumen wall and a sphincter, the method comprising:

providing a balloon catheter comprising an elongated catheter extending between a proximal end and a distal end, and an inflatable element defining a hollow interior region when inflated located on the catheter, the inflatable element being adapted for locating in the one of the vessel, the lumen and the sphincter, locating the inflatable element of the balloon catheter in the one of the vessel, the lumen and the sphincter, inflating the inflatable element to one of a pressure and a transverse cross-sectional area adjacent a portion of the one of the vessel wall, the lumen wall and the sphincter, at which the distensibility is to be determined, sufficient to distend the one of the vessel wall, the lumen wall and the sphincter, determining the other of the pressure and the transverse cross-sectional area adjacent the portion of the one of the vessel wall, the lumen wall and the sphincter, at which the distensibility is to be determined when the inflatable element is inflated to the one of the pressure and the transverse cross-sectional area sufficient to distend the one of the vessel wall, the lumen wall and the sphincter, and determining the distensibility of the one of the vessel wall, the lumen wall and the sphincter as a function of one of the transverse cross-sectional area of the inflatable element adjacent the portion of the one of the vessel wall, the lumen wall and the sphincter, at which the distensibility is to be determined and the corresponding pressure of the inflating medium in the inflatable element when the inflatable element is inflated to the one of the pressure and the transverse cross-sectional area sufficient to distend the one of the vessel wall, the lumen wall and the sphincter.

Preferably, the distensibility of the one of the vessel wall, the lumen wall and the sphincter is determined as a function of the transverse cross-sectional area of the inflatable element adjacent the portion of the one of the vessel wall, the lumen wall and the sphincter, at which the distensibility is to be determined.

In one embodiment of the invention the distensibility of the one of the vessel wall, the lumen wall and the sphincter is determined as a function of the ratio of the transverse cross-sectional area of the inflatable element adjacent the portion of the one of the vessel wall, the lumen wall and the sphincter, at which the distensibility is to be determined to the corresponding pressure of the inflating medium in the inflatable element.

In one embodiment of the invention the distensibility of the one of the vessel wall, the lumen wall and the sphincter is determined as a function of one of the transverse cross-sectional area of the inflatable element adjacent the portion of the one of the vessel wall, the lumen wall and the sphincter, at which the distensibility is to be determined, and the pressure of the inflating medium in the inflatable element when the inflatable element is inflated to one of a first pressure and a first transverse cross-sectional area adjacent the portion of the one of the vessel wall, the lumen wall and the sphincter, at which the distensibility of which is to be determined.

Preferably, the distensibility of the one of the vessel wall, the lumen wall and the sphincter is determined as the value of the transverse cross-sectional area of the inflatable element adjacent the portion of the one of the vessel wall, the lumen wall and the sphincter, the distensibility of which is to be determined when the inflatable element is inflated to the first pressure.

In another embodiment of the invention the distensibility of the one of the vessel wall, the lumen wall and the sphincter is determined as a function of two values of the transverse cross-sectional area of the inflatable element adjacent the portion of the one of the vessel wall, the lumen wall and the sphincter, at which the distensibility is to be determined and two values of the pressure of the inflating medium in the inflatable element corresponding to the two values of the transverse cross-sectional area thereof.

In one embodiment of the invention the distensibility of the one of the vessel wall, the lumen wall and the sphincter is determined as a function of the ratio of the difference between the two values of the transverse cross-sectional area of the inflatable element adjacent the portion of the one of the vessel wall, the lumen wall and the sphincter, at which the distensibility is to be determined to the difference between the two corresponding values of the pressure of the inflating medium in the inflatable element.

In another embodiment of the invention the distensibility of the one of the vessel wall, the lumen wall and the sphincter is determined as a function of an equation of a line containing two values of the transverse cross-sectional area of the inflatable element adjacent the portion of the one of the vessel wall, the lumen wall and the sphincter, at which the distensibility is to be determined and the two values of the pressure of the inflating medium in the inflatable element corresponding to the two values of the transverse cross-sectional area thereof, the line being a plot of the transverse cross-sectional area of the inflatable element adjacent the portion of the one of the vessel wall, the lumen wall and the sphincter, at which the distensibility is to be determined against the corresponding pressure of the inflating medium in the inflatable element.

Preferably, the distensibility of the one of the vessel wall, the lumen wall and the sphincter is determined in the form of a distensibility index, the distensibility index being a function of the value of a point of intersection of the axis on which one of the transverse cross-sectional area and the pressure is plotted by the line containing the two values of the transverse cross-sectional area of the inflatable element and the corresponding pressures of the inflating medium in the inflatable element.

Advantageously, the distensibility index of the one of the vessel wall, the lumen wall and the sphincter is determined as a function of the value of the point of intersection of the axis on which the transverse cross-sectional area of the inflatable element is plotted by the line containing the two values of the transverse cross-sectional area of the inflatable element and the corresponding pressures of the inflating medium in the inflatable element.

In one embodiment of the invention the distensibility of the one of the vessel wall, the lumen wall and the sphincter is determined as a function of the equation of the line containing the two values of the transverse cross-sectional area of the inflatable element adjacent the portion of the one of the vessel wall, the lumen wall and the sphincter, at which the distensibility is to be determined and the two corresponding values of the pressure of the inflating medium in the inflatable element when the inflatable element is inflated to one of a first pressure and a second pressure and a first transverse cross-sectional area and a second transverse cross-sectional area adjacent the portion of the one of the vessel wall, the lumen wall and the sphincter, at which the distensibility is to be determined.

Preferably, the inflatable element is inflated to the one of the first pressure and the first transverse cross-sectional area prior to being inflated to the one of the second pressure and the second transverse cross-sectional area, the first pressure and the first transverse cross-sectional area being less than the second pressure and the second transverse cross-sectional area, respectively.

In one embodiment of the invention the value of the one of the pressure and the transverse cross-sectional area to which the inflatable element is inflated to determine the distensibility of the one of the vessel wall, the lumen wall and the sphincter is a value at which the relationship between the transverse cross-sectional area of the inflatable element adjacent the portion of the one of the vessel wall, the lumen wall and the sphincter, at which the distensibility is to be determined and the pressure of the inflating medium in the inflatable element is a linear relationship.

In an alternative embodiment of the invention the distensibility of the one of the vessel wall, the lumen wall and the sphincter is determined as a function of one of the transverse cross-sectional area of the inflatable element adjacent the portion of the one of the vessel wall, the lumen wall and the sphincter, at which the distensibility is to be determined and the pressure of the inflating medium in the inflatable element at a point at which the relationship between the transverse cross-sectional area of the inflatable element and the pressure of the inflating medium in the inflatable element transitions from being a substantially linear relationship to a substantially non-linear relationship.

In another embodiment of the invention the inflatable element is provided as an elongated inflatable element extending between a proximal end and a distal end and is adapted for locating in a sphincter with the sphincter located intermediate the proximal end and the distal end thereof for determining the distensibility of the sphincter, so that when the inflatable element is inflated, the sphincter shapes the inflatable element to define a portion of minimum transverse cross-sectional area adjacent the sphincter, and the distensibility of the sphincter is determined as a function of a value of one of the transverse cross-sectional area of the inflatable element adjacent the portion of minimum transverse cross-sectional area and the pressure of the inflating medium in the inflatable element when the inflatable element is inflated to the pressure sufficient to distend the sphincter.

Ideally, the inflatable element is located in the sphincter so that the sphincter is located substantially mid-way between the proximal end and the distal end of the inflatable element.

Figure 2:
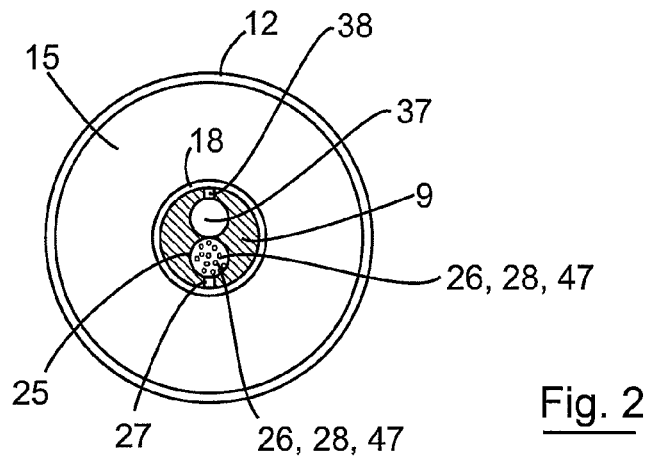
Figure 3:
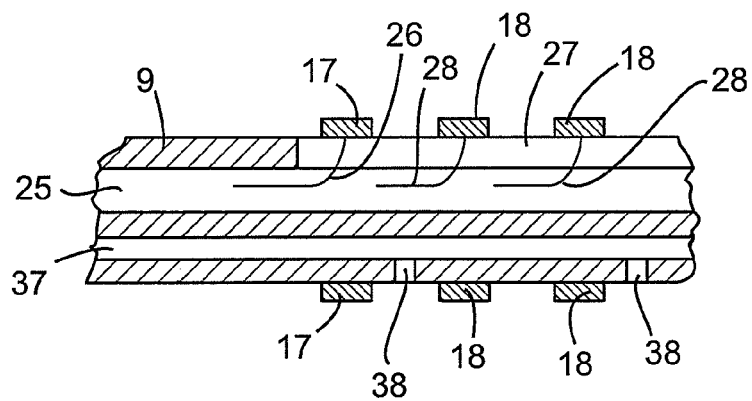
Figure 4:
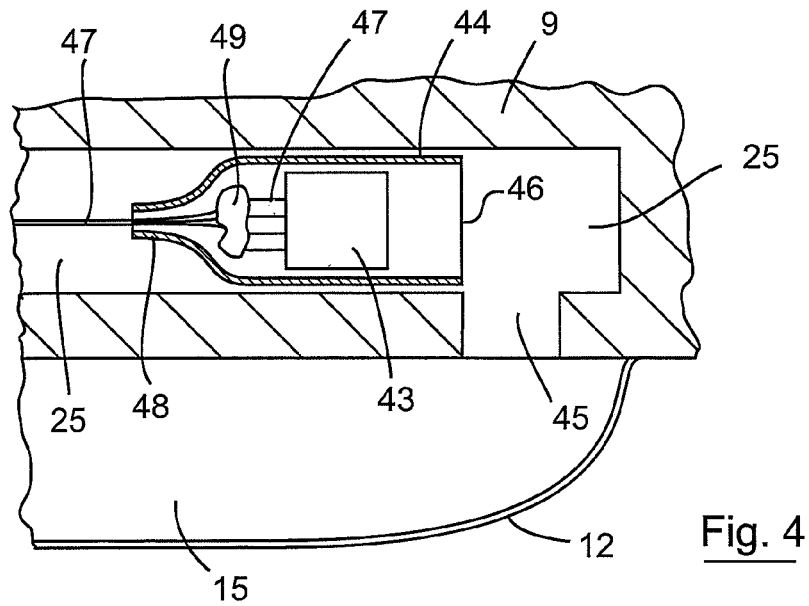
Figure 5:
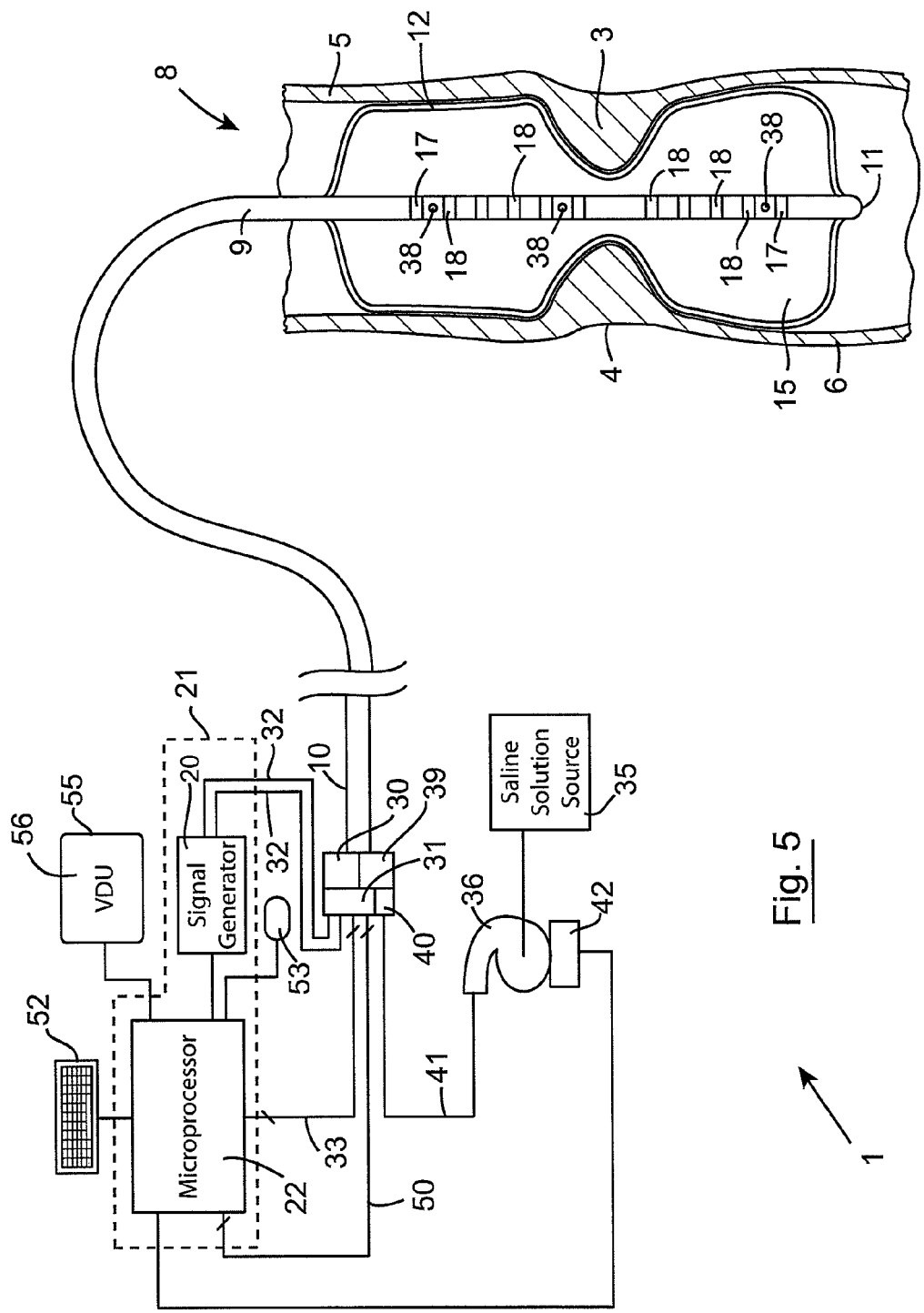
Figure 6:
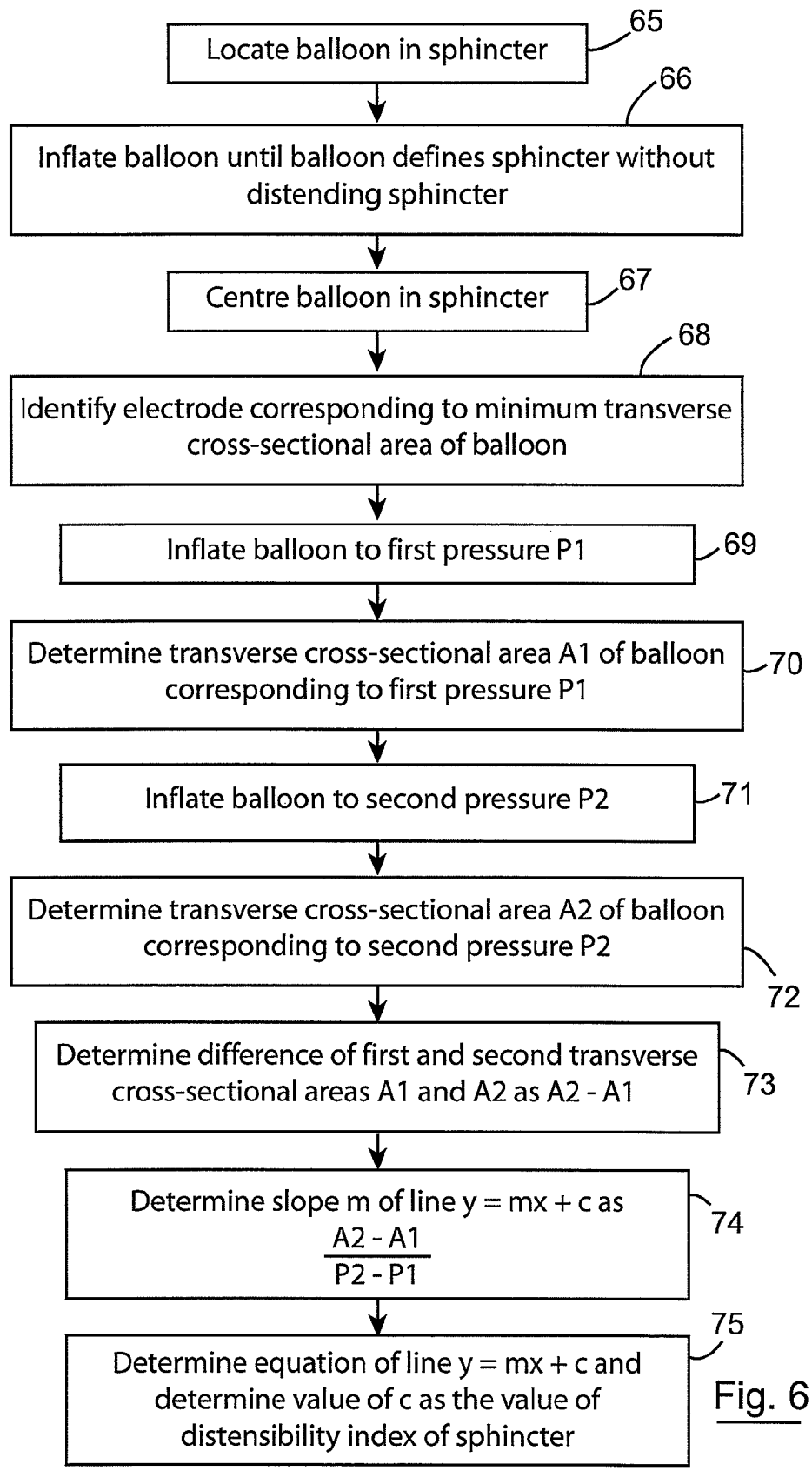
Figure 7:
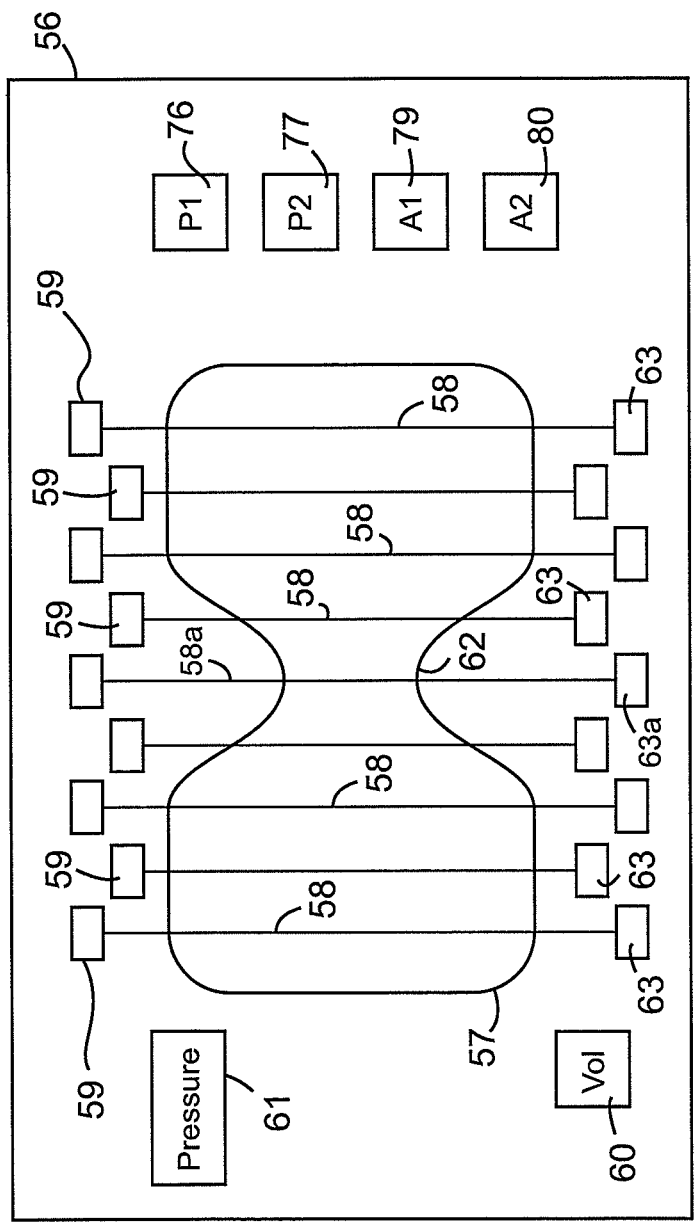
Figure 8:
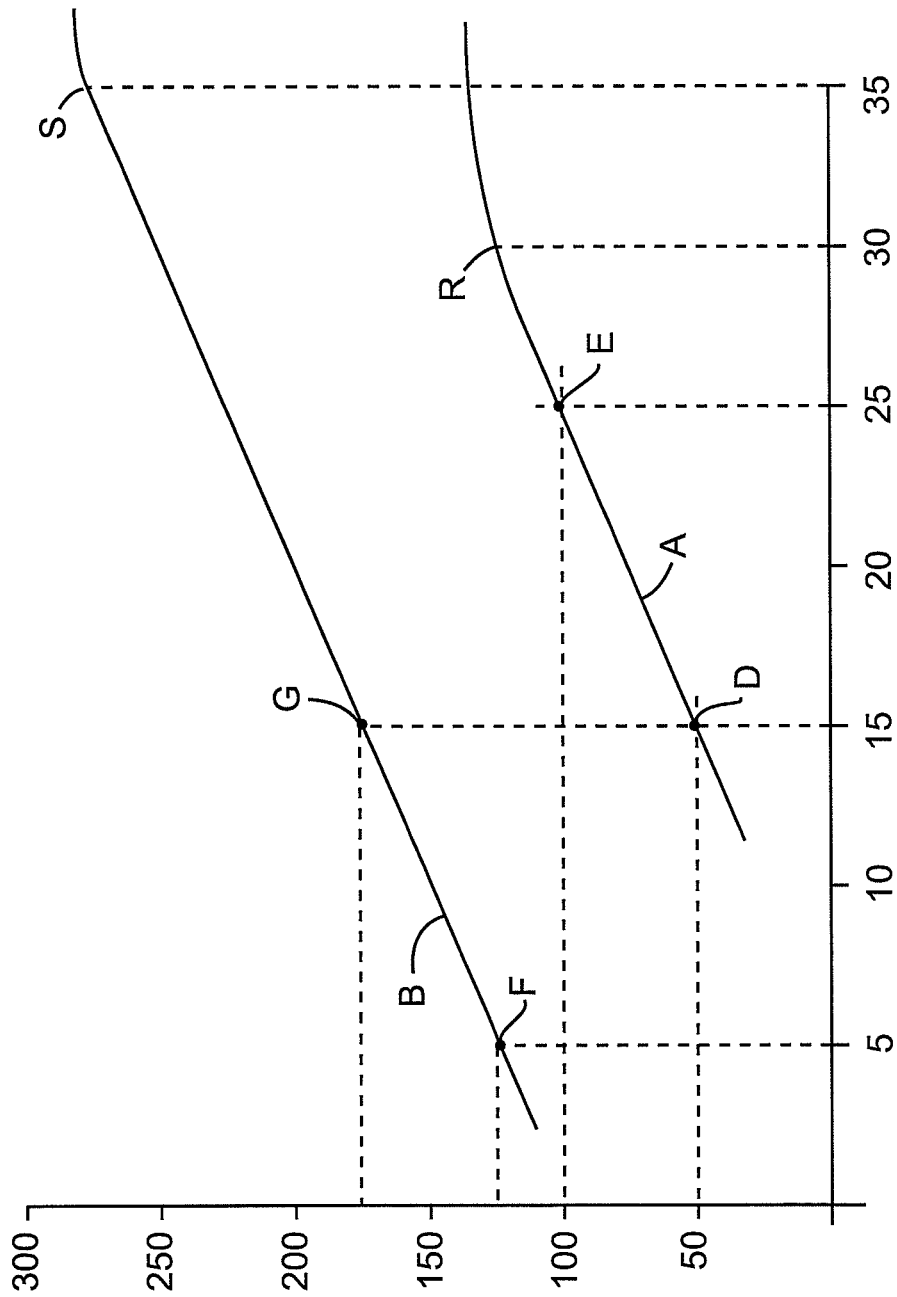
Figure 9:
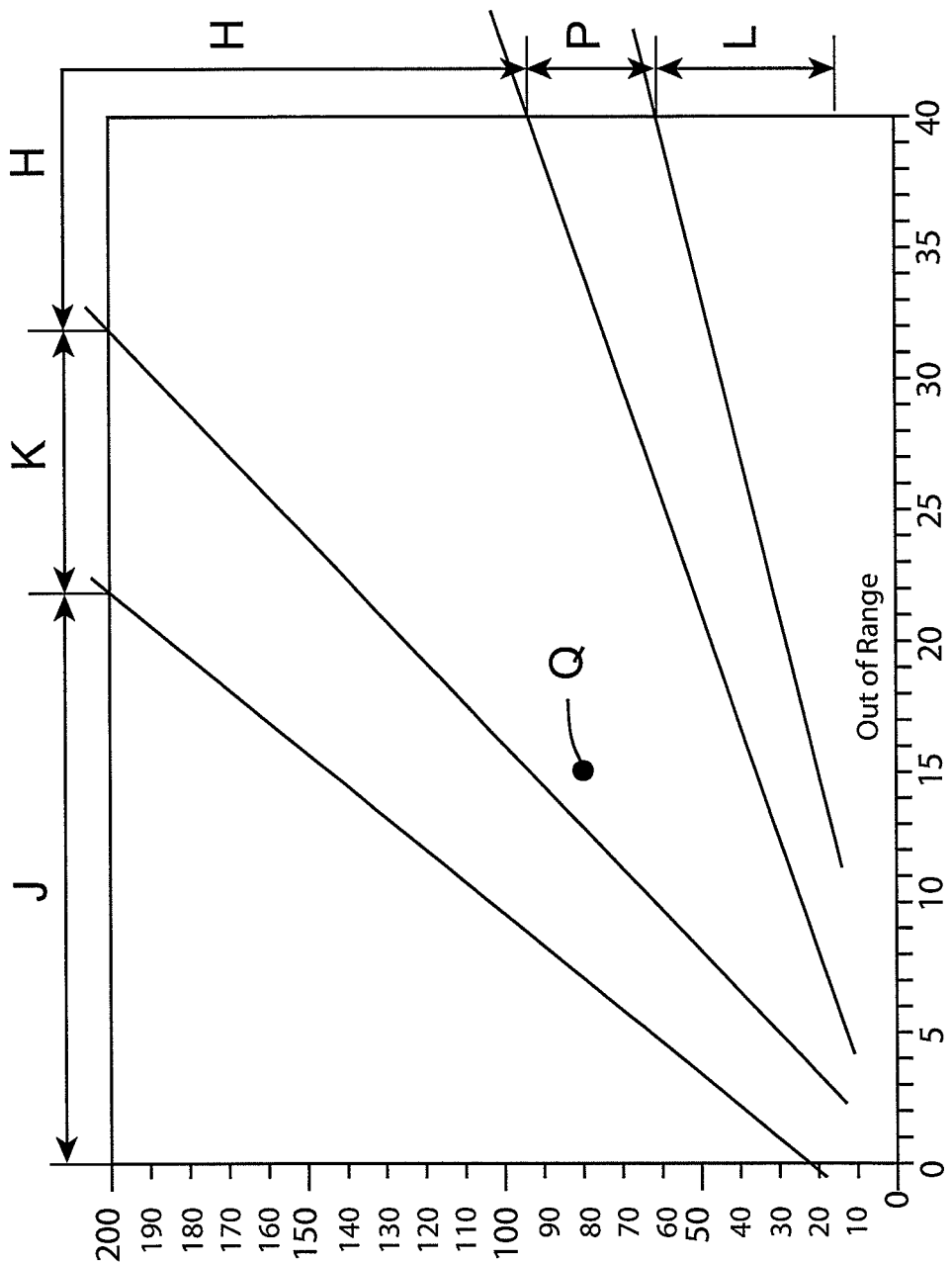

The invention will be more clearly understood from the following description of some preferred embodiment thereof, which are given by way of example only, with reference to the accompanying drawings, in which:

FIG. 1 is a schematic view of apparatus according to the invention for determining the distensibility of a vessel, lumen or sphincter, FIG. 2 is a transverse cross-sectional end elevational view of a portion of the apparatus of FIG. 1 on the line II-II of FIG. 1, FIG. 3 is a cross-sectional side elevational view of a detail of the apparatus of FIG. 1, FIG. 4 is a cross-sectional side elevational view of another detail of the apparatus of FIG. 1, FIG. 5 is a schematic view of the apparatus of FIG. 1 illustrating the apparatus in use, FIG. 6 is a flowchart of a method according to one embodiment of the invention for determining the distensibility of a vessel, lumen or sphincter, FIG. 7 is a front elevational view of another portion of the apparatus of FIG. 1, FIG. 8 is a graphical representation of the performance of two lower oesophageal sphincters under outwardly distending pressure, and FIG. 9 is a graphical representation of the distensibility of a lower oesophageal sphincter.

Referring to the drawings, and initially to FIGS. 1 to 7, there is illustrated apparatus according to the invention, indicated generally by the reference numeral 1, for determining the distensibility of a vessel, a lumen or a sphincter, and in particular, for determining the distensibility of a sphincter or of the wall of a vessel or a lumen. In FIG. 5 the apparatus 1 is illustrated in use for determining the distensibility of a lower oesophageal sphincter 3 which is located at a junction 4 between an oesophagus 5 and a stomach 6 of a human subject. By determining the distensibility of a lower oesophageal sphincter, an assessment of the tone of the muscles of the sphincter may be made, and in turn an assessment of gastroesophageal reflux disease (GERD) in a subject may be made as well as an assessment of other conditions and diseases, such as achalasia. In this particular embodiment of the invention the distensibility of the sphincter 3 is determined as a distensibility index as will be described in detail below. For ease of understanding the invention, the apparatus 1 will be described herein for use in determining the distensibility of the lower oesophageal sphincter 3. However, it will be readily apparent to those skilled in the art that the apparatus 1 may be used for determining the distensibility of any other sphincter in a human or animal subject, and may also be used for determining the distensibility of the wall of a vessel or lumen in a human or animal subject. Before describing the operation of the apparatus for determining the distensibility of the lower oesophageal sphincter 3, the apparatus 1 will first be described.

The apparatus 1 comprises a balloon catheter 8 comprising an elongated catheter 9 extending from a proximal end 10 to a distal end 11. An inflatable element, in this embodiment of the invention an elongated balloon 12 is located on the catheter 9 towards the distal end 11 thereof. The balloon 12 extends between a proximal end 13 and a distal end 14 and is of a compliant material and inflates to a cylindrical configuration. The catheter 9 extends through the balloon 12 and the balloon 12 when inflated defines with the catheter 9 an annular hollow interior region 15.

A measuring means, for measuring the transverse cross-sectional area of the balloon 12 at a plurality of axially spaced apart locations, in this embodiment of the invention, comprises a pair of axially spaced apart stimulating electrodes 17 located on the catheter 9 within the balloon 12 for receiving a stimulating signal, which in this embodiment of the invention is a constant current signal of known current value. A plurality of axially spaced apart sensing electrodes 18 are located on the catheter 9 between the stimulating electrodes 17 and axially spaced apart therefrom for producing response signals in response to the stimulating current signal applied to the stimulating electrodes 17 when the balloon 12 is inflated with an electrically conductive inflating medium, such as a saline solution. The response signals produced on the sensing electrodes 18 in response to the stimulating current signal applied to the stimulating electrodes 17 are indicative of the values of the transverse cross-sectional area of the balloon 12 adjacent the respective sensing electrodes 18. Where the sphincter, vessel or lumen, the distensibility of which is to be determined is of circular transverse cross-sectional area, as in the case of the lower oesophageal sphincter, the signals produced on the sensing electrodes 18 are also indicative of the diameter of the balloon 12 adjacent the respective sensing electrodes 18. A signal generating means, namely, a signal generator 20 located in and controlled by a control means, namely, a control circuit 21 produces the stimulating constant current signal which is applied to the stimulating electrodes 17.

The control circuit 21 comprises a signal processing means and a computing means, namely, a microprocessor 22 which is programmed to operate the signal generator 20 at appropriate times for applying the stimulating current signal to the stimulating electrodes 17. The microprocessor 22 is programmed to function as a computing means to read the response signals from the sensing electrodes 18, and to compute the values of the transverse cross-sectional area of the balloon 12 at locations adjacent the respective sensing electrodes 18, and in turn to determine the distensibility of the lower oesophageal sphincter, as will be described below. The determination of the transverse cross-sectional area of a balloon of a balloon catheter comprising stimulating and sensing electrodes similar to the stimulating and sensing electrodes 17 and 18 of the balloon catheter 8 adjacent the respective sensing electrodes is described in PCT Published Application Specification No. WO 2009/001328.

A wire accommodating lumen 25 extending through the catheter 9 from the proximal end 10 thereof to the balloon 12 accommodates a pair of mutually insulated electrically conductive wires 26 from the proximal end 10 of the catheter 9 to the respective stimulating electrodes 17, see FIG. 3, although only one wire 26 is illustrated in FIG. 3. An elongated wire accommodating slot 27 extending longitudinally along the catheter 9 within the balloon 12 accommodates the wires 26 from the wire accommodating lumen 25 to the stimulating electrodes 17. Mutually insulated electrically conductive wires 28 extend through the wire accommodating lumen 25 from the proximal end 10 of the catheter 9 through the wire accommodating slot 27 to the sensing electrodes 18. The wires 26 and 28 terminate in a socket illustrated in block representation by a block 30 at the proximal end 10 of the catheter 9. A plug also illustrated in block representation by a block 31 is releasably coupleable to the socket 30, and a pair of mutually insulated electrically conductive wires 32 extend from the plug 31 to the signal generator 20 for coupling the wires 26 from the stimulating electrodes 17 to the signal generator 20. Wires represented by a bus 33 coupled between the plug 31 and the microprocessor 22 couple the wires 28 from the sensing electrodes 18 to the microprocessor 22.

In this embodiment of the invention the electrically conductive inflating medium is an electrically conductive liquid inflating medium, namely, a saline solution, and is provided from a saline solution source 35. A pump 36 pumps the saline solution from the source 35 to the balloon 12 for inflating thereof, and from the balloon 12 to the source 35 for deflating the balloon 12. A communicating means comprising an inflating medium accommodating lumen 37 extends through the catheter 9 from the proximal end 10 thereof to the balloon 12 and communicates with the balloon 12 through a plurality of radial ports 38 extending through the catheter 9 from the lumen 37, see FIG. 3. The inflating medium accommodating lumen 37 terminates at the proximal end 10 of the catheter 9 in a coupling element which is represented by a block 39 at the proximal end 10 of the catheter 9. A corresponding coupling element represented by a block 40 is releasably coupled to the coupling element 39, and couples the pump 36 to the inflating medium accommodating lumen 38 through a pipe 41.

The pump 36 may be any suitable pump, for example, a peristaltic pump or a piston pump, for example, or a syringe or any other suitable pump. An electrically powered motor 42 operates the pump 36 for pumping the inflating medium between the source 35 and the balloon 12 for inflating and deflating the balloon 12. The motor 42 is powered under the control of the microprocessor 22 for both inflating and deflating the balloon 12.

A pressure sensing means comprising a pressure sensor 43 for monitoring the pressure of the inflating medium in the balloon 12 and for producing signals indicative of the pressure of the inflating medium in the balloon 12 for reading by the microprocessor 22 is located in the catheter 9 in the wire accommodating lumen 25 within the hollow interior region 15 of the balloon 12, see FIG. 4. The pressure sensor 43 in this embodiment of the invention is a strain gauge implemented as a solid state device, and is housed in a non-deformable protective housing 44 within the wire accommodating lumen 25. The housing 44 is of a rigid plastics material formed by injection moulding in order to avoid any danger of any portion of the housing 44 bearing on the pressure sensor 43 as a result of bending or squeezing of the catheter 9 which would otherwise result in a spurious pressure reading being produced by the pressure sensor 43. A port 45 extending from the wire accommodating lumen 25 adjacent the distal end thereof communicates the wire accommodating lumen 25 with the hollow interior region 15 of the balloon 12. The housing 44 terminates in an opening 46 which communicates the pressure sensor 43 with the hollow interior region 15 of the balloon 12 through the port 45, so that the pressure sensor 43 is subjected directly to the pressure of the inflating medium in the hollow interior region 15 of the balloon 12.

Wires 47 from the pressure sensor 43 extend through an outlet 48 in the housing 44, and are accommodated through the wire accommodating lumen 25 to the proximal end 10 of the catheter 9. Adhesive 49 secures the wires 47 and in turn the pressure sensor 43 in the housing 44. The wires 47 from the pressure sensor 43 terminate in the socket 30 at the proximal end 10 of the catheter 9. A bus 50 extending between the plug 31 and the microprocessor 22 couples the wires 47 from the pressure sensor 43 to the microprocessor 22 for facilitating reading of the signals from the pressure sensor 43 indicative of the pressure of the inflating medium in the balloon 12 by the microprocessor 22.

A keyboard 52 coupled to the microprocessor 22 facilitates inputting of commands and data to the microprocessor 22. A mouse 53 coupled to the microprocessor 22 also facilitates inputting commands and data to the microprocessor 22.

A visual display unit 55 having a visual display screen 56 is coupled to the microprocessor 22, and is operated under the control of the microprocessor 22 for displaying a graphical representation 57 of a longitudinal cross-section of the balloon 12 as the balloon 12 is being inflated and deflated. A typical graphical representation 57 of the balloon 12 for determining the distensibility of the lower oesophageal sphincter 3 is illustrated in FIG. 7. The microprocessor 22 is programmed to prepare the graphical representation 57 of the balloon 12 from the values of the transverse cross-sectional area of the balloon 12 adjacent the respective sensing electrodes 18. The microprocessor 22 is also programmed to display an indication of the location of the sensing electrodes 18 relative to the graphical representation 57 of the balloon 12 on the screen 56. In this embodiment of the invention the indication of the location of the sensing electrodes 18 is produced by a graphical representation of the sensing electrodes 18 provided by lines 58 which are representative of the sensing electrodes 18 superimposed on the graphical representation 57 of the balloon 12. Windows 59 corresponding to the lines 58 display the current values of the transverse cross-sectional area of the balloon 12 adjacent the sensing electrodes 18. Windows 63 also corresponding to the lines 58 are provided for displaying the distensibility of the lower oesophageal sphincter as will be described below, which in this embodiment of the invention is a distensibility index. A window 60 displays the current volume to which the balloon 12 is inflated. The current pressure of the inflating medium within the balloon 12 is displayed in a window 61 on the display screen.

Referring now to FIG. 8, a plot of the performance of two lower oesophageal sphincters when subjected to a radially outward pressure is illustrated. The transverse cross-sectional area of the sphincters is plotted on the vertical Y-axis, and the pressure is plotted on the horizontal X-axis. Graph A represents the performance of a healthy lower oesophageal sphincter, while Graph B represents a GERD lower oesophageal sphincter. Both Graphs A and B were obtained by placing the balloon 12 of the balloon catheter 8 in the relevant sphincters, with the sphincter located substantially midway along the balloon 12 between the proximal end 13 and the distal end 14. Since the thickness of the skin of the balloon 12 is minimal, the transverse cross-sectional area of each sphincter was determined as being the internal transverse cross-sectional area of the balloon 12 at the location at which the transverse cross-sectional area of the balloon 12 was a minimum, in other words, at the necked portion 62, and was obtained by computing the transverse cross-sectional area of the balloon from the response signal produced on the sensing electrode adjacent the necked portion 62 of the balloon 12 at corresponding pressure values of the inflating medium in the balloon 12. If the skin of the balloon 12 was of a thicker material, the thickness of the material of the balloon 12 would be taken into account when computing the transverse cross-sectional area of the necked portion 62 of the balloon 12.

Initially as the balloon 12 was being inflated in both sphincters, the pressure remained substantially constant until the balloon 12 defined the relevant sphincter without distending the sphincter, in other words, until the balloon 12 was inflated to the general hourglass configuration illustrated in FIGS. 5 and 7 with the sphincter forming the necked portion 62 of the balloon 12 in its non-distended state. Thereafter as more inflating medium was pumped into the balloon 12, the pressure in the balloon 12 commenced to increase, thus acting on the relevant sphincter to cause the sphincter to distend.

The relationship between the transverse cross-sectional area of a lower oesophageal sphincter and the pressure to which it is subjected approximates to an exponential relationship. Initially as the pressure commenced to increase, and the sphincter commences to distend, the relationship between the transverse cross-sectional area of each sphincter and the pressure of the inflating medium within the balloon is a linear relationship, and in the case of the healthy sphincter 3 of graph A continues to be a linear relationship until the pressure of the inflating medium in the balloon 12 reaches a pressure of approximately 30 mm of mercury, at which stage the relationship becomes non-linear. In the case of the GERD oesophageal sphincter of graph B, the relationship between the transverse cross-sectional area of the sphincter and the pressure of the inflating medium in the balloon 12 continues to be a linear relationship until the pressure of the inflating medium in the balloon 12 reaches a pressure of approximately 35 mm of mercury, at which stage the relationship becomes non-linear. In this embodiment of the invention the distensibility index of the two sphincters of graphs A and B are determined from the values of the transverse cross-sectional area of the sphincter and the corresponding pressure of the inflating medium in the balloon 12, while the relationship between the transverse cross-sectional area of the sphincter and the pressure of the inflating medium in the balloon 12 is linear. In accordance with the method according to this embodiment of the invention, the dispensability index of each sphincter is determined by inflating the balloon 12 to two pressures, namely, a first pressure and a second pressure in the linear part of the relationship of graphs A and B.

In the case of the healthy lower oesophageal sphincter, the balloon 12 is initially inflated to a first pressure of 15 mm of mercury, which results in the sphincter being distended to a transverse cross-sectional area of approximately 50 mm$^2$, namely point D on Graph A. The balloon 12 is then inflated to a second pressure of 25 mm of mercury, which results in the sphincter being distended to a transverse cross-sectional area of approximately 100 mm$^2$, namely point E on graph A. In the case of the GERD sphincter, the balloon 12 is inflated to a first pressure of approximately 5 mm of mercury, which results in the GERD sphincter being distended to a transverse cross-sectional area of approximately 125 mm$^2$, namely, point F on graph B. Increasing the pressure within the balloon 12 to a second pressure of 15 mm of mercury results in the GERD sphincter being distended to a transverse cross-sectional area of approximately 175 mm$^2$, namely point G on graph B.

However, it can be seen from the Graphs A and B of the two sphincters that in this particular case the slopes of the respective Graphs A and B are substantially similar, the difference being that the Graph B of the GERD sphincter is shifted upwardly relative to Graph A of the healthy sphincter, and also is shifted to the left of Graph A of the healthy sphincter. This upward shift in the graph of a GERD sphincter relative to the graph of a healthy sphincter is made use of in operating the apparatus 1 according to this embodiment of the invention to determine firstly if a lower oesophageal sphincter is a GERD sphincter, and the degree to which the GERD sphincter is diseased.

By taking the equation of a line as follows:

$$y=mx+c,$$

where y represents the transverse cross-sectional area of the sphincter, x represents the pressure of the inflating medium within the balloon to which the balloon which is located in the sphincter is inflated, m represents the slope of the line, and c represents the point of intersection of the Y-axis by the line of the graphs A and B, and by determining the value of c, the upward shift in the graph of a GERD sphincter from that of a healthy sphincter can be determined. It is the value of c which is determined to be the distensibility index of a sphincter. By comparing the value of the distensibility index c of a sphincter with a standard distensibility index c of a healthy sphincter, an assessment can be made of the condition of the sphincter, and whether the sphincter is a diseased sphincter or otherwise. An upward shift in the graph of the equation y=mx+c, which is indicated by an increase in the value of the distensibility index c above the value of the distensibility index c for a healthy sphincter is indicative of a relatively loose sphincter, which results in GERD. The amount by which the distensibility index c of the sphincter is above the distensibility index c of a healthy sphincter is indicative of the looseness of the sphincter, and in turn the seriousness of the GERD condition. A value of the distensibility index c below the value of the distensibility index c of a healthy sphincter is indicative of a relatively tight sphincter, which would result from an achalasia condition, and the amount by which the distensibility index c of the sphincter is below the value of the distensibility index c of a healthy sphincter is indicative of the tightness of the sphincter, and in turn the seriousness of the achalasia condition.

Accordingly, the method according to this embodiment of the invention employed in using the apparatus 1 for determining the distensibility of the lower oesophageal sphincter 3 will now be described with reference to FIG. 6. Initially the distal end 11 of the balloon catheter 8 is inserted into the oesophagus 5 either nasally or orally, and the balloon catheter 8 is advanced through the oesophagus 5 until the balloon 12 is located in the sphincter 3 with the sphincter 3 approximately midway along the balloon 12 between the proximal end 13 and the distal end 14, see block 65. With the balloon 12 located in the sphincter 3, the microprocessor 22 in response to a command entered through the keyboard 52 or the mouse 53 operates the motor 42 to power the pump 36 for inflating the balloon 12. The microprocessor 22 is programmed to read signals from the pressure sensor 43 for determining the pressure of the inflating medium in the balloon 12 as the balloon is being inflated. The microprocessor 22 is also programmed to operate the signal generator 20 to apply the constant current stimulus signal to the stimulating electrodes 17 and to read the resulting response signals produced on the sensing electrodes 18 as the balloon 12 is being inflated. The microprocessor 22 is programmed to compute the values of the transverse cross-sectional area of the balloon 12 at locations corresponding to the locations of the sensing electrodes 18 from the response signals read from the sensing electrodes 18, and to continuously update the values of the transverse cross-sectional area of the balloon 12 adjacent the sensing electrodes 18. The values of the transverse cross-sectional area of the balloon 12 adjacent the respective sensing electrodes 18 are displayed in the corresponding windows 59, and are continuously updated.

The microprocessor 22 is programmed to continue operating the pump 36 to inflate the balloon 12 until the balloon 12 has been inflated to a state where a portion of the balloon 12 defines the sphincter 3 without distending the sphincter 3, see block 66. It has been found that the pressure of the inflating medium in the balloon 12 remains substantially constant until the balloon 12 has been inflated to just define the sphincter 3 and the adjacent portions of the oesophagus 5 and stomach 6. At that stage the pressure of the inflating medium in the balloon 12 commences to increase. The microprocessor 22 is programmed to monitor the pressure signals read from the pressure sensor 43 to determine when the pressure of the inflating medium in the balloon 12 commences to increase, thus indicating that the balloon 12 has been inflated to define the sphincter 3 without distending the sphincter 3. Alternatively, the point at which the balloon 12 defines the sphincter 3 without distending the sphincter 3 may be determined by observing the representation 57 of the balloon 12 on the screen 56 and by observing the pressure of the inflating medium in the balloon 12 displayed in the window 61.

Once the balloon 12 has been inflated to just define the sphincter 3, if it appears from the representation 57 of the balloon 12 on the screen 56 that the sphincter 3 is not centrally located axially on the balloon 12, the balloon catheter 8 is manoeuvred so that the balloon 12 is located in the sphincter 3 with the sphincter 3 substantially centrally axially located on the balloon 12, see block 67. The manoeuvring of the balloon 12 in the sphincter 3 can be visually observed from the graphical representation 57 of the balloon 12 displayed on the visual display screen 56. The location of the sphincter 3 on the balloon 12 is identified by the necked portion 62 of the representation 57, and in this case is located adjacent the sensing electrode 18 represented by the line 58$a$ on the screen 56 of FIG. 7.

The microprocessor 22 is programmed to determine the sensing electrode 18 which coincides with the minimum transverse cross-sectional area of the sphincter. This is the sensing electrode 18 which is represented by the line 58$a$ in the necked portion 62 of the representation 57 of the sphincter 3 in FIG. 7, see block 68. The necked portion 62 of the balloon 12 may be determined by the microprocessor 22 by a curve fitting programme or by comparing the computed values of the transverse cross-sectional area of the balloon 12 adjacent the respective sensing electrodes 18 in order to determine the electrode 18 at which the transverse cross-sectional area of the balloon 12 is of minimum value.

The microprocessor 22 is programmed to inflate the balloon 12 to a first pressure P1, see block 69, once the sensing electrode 18 which corresponds to the line 58$a$ has been identified. The first pressure P1 of value sufficient to cause the sphincter to distend. During the inflating of the balloon 12 to the first pressure P1 the microprocessor 22 reads the signals from the pressure sensor 43. When the signals from the pressure sensor 43 are indicative of the pressure of inflating medium in the balloon 12 being at the first pressure P1, the microprocessor 22 reads the signal on the sensing electrode 18 adjacent the necked portion 62 of the balloon 12 and computes and saves the transverse cross-sectional area A1 of the balloon 12 at that sensing electrode 18, see block 70. The transverse cross-sectional area of the balloon 12 read from the sensing electrode 18 adjacent the necked portion 62 of the balloon 12 corresponds to the transverse cross-sectional area A1 of the sphincter 3 at the first pressure P1.

The microprocessor 22 then operates the pump 36 to continue to inflate the balloon 12 until the pressure determined from the signals read from the pressure sensor 43 are indicative of the balloon 12 being inflated to a second pressure P2, see block 71. The second pressure P2 is greater than the first pressure P1. When the microprocessor 22 determines that the balloon 12 has been inflated to the second pressure P2, the microprocessor 22 reads the signals on the sensing electrode 18 adjacent the necked portion 62 of the balloon 12 and computes and saves the value of the transverse cross-sectional area A2 of the balloon 12 at that sensing electrode 18, see block 72. This is the transverse cross-sectional area A2 of the sphincter 3 at the second pressure P2.

The first and second pressures P1 and P2 are selected to be of values within the range of pressure values of the inflating medium in the balloon 12 where the relationship between the transverse cross-sectional area of the sphincter and the pressure of the inflating medium in the balloon 12 is a linear relationship. The first and second pressures may be either pre-entered and stored in the microprocessor 22, or entered into the microprocessor 22 by a surgeon or physician operating the apparatus 1 prior to commencing inflating of the balloon 12. In the case of a suspected healthy sphincter, the first pressure is selected typically to be in the range of 15 mm of mercury to 20 mm of mercury, and the second pressure is typically selected to be in the range of 20 mm of mercury to 25 mm of mercury. In the case of a suspected GERD sphincter, the first pressure typically is selected to be in the order of 5 mm of mercury to 10 mm of mercury, and the second pressure is selected to be in the range of 10 mm of mercury to 15 mm of mercury.

Alternatively, the microprocessor 22 may be programmed to progressively increase the pressure of the inflating medium in the balloon 12 while continuously reading signals from the electrode 18 adjacent the necked portion 62 of the balloon 12 in order to determine the pressure of the inflating medium in the balloon 12 at which the relationship between the signals read from the sensing electrode 18 adjacent the necked portion 62 of the balloon and the pressure of the inflating medium in the balloon 12 transition from being a linear relationship to a non-linear relationship. The pressure range over which the relationship between the transverse cross-sectional area of the sphincter and the pressure is a linear relationship can then be determined. Once the pressure range over which the relationship between the transverse cross-sectional area of the sphincter and the pressure of the inflating medium in the balloon 12 is a linear relationship has been determined, the microprocessor 22 could then also be programmed to select the first and second pressures towards the lower and upper extreme pressure values over which the relationship between the transverse cross-sectional area of the sphincter and the pressure of the inflating medium in the balloon 12 remains linear.

Having determined and saved the transverse cross-sectional areas A1 and A2 of the sphincter 3 which correspond to the first and second pressures P1 and P2, the microprocessor 22 computes the difference of the two transverse cross-sectional areas A2 and A1, see block 73 where the microprocessor 22 subtracts the area A1 corresponding to the first pressure P1 from the area A2 corresponding to the second pressure P2. The microprocessor 22 is programmed to then compute the slope m of a line y=mx+c representative of the linear portion of a graph containing the points which correspond to the transverse cross-sectional area A1 and the first pressure P1, and the transverse cross-sectional area A2 and the second pressure P2, respectively. The microprocessor 22 computes the slope m of the line by computing the ratio of the difference of the two transverse cross-sectional areas A1 and A2 to the difference of the first and second pressures P1 and P2, see block 74. Thus, the microprocessor 22 subtracts the value of the first pressure P1 from the second pressure P2 and divides the difference of the areas A2 and A1 of the sphincter 3 by the difference of the first and second pressures P2 and P1.

With the slope m of the line y=mx+c computed, the microprocessor 22 is programmed to determine the equation of the line y=mx+c, and from this the microprocessor 22 is programmed to compute the value of the distensibility index c from the equation of the line y=mx+c, see block 75. The value of the distensibility index c is the point of intersection of the Y-axis by the line y=mx+c representative of the transverse cross-sectional area/pressure relationship of the sphincter 3 with the balloon pressure. In other words, the value c is the theoretical value of the transverse cross-sectional area of the sphincter 3 at a pressure P equal to zero. The distensibility index of the sphincter is determined as the value c of the line y=mx+c, and is displayed in the window 63$a$ in the visual display screen 56 adjacent the necked portion 62 of the graphical representation of the balloon 12.

Windows 76 and 77 are provided in the visual display screen 56 in which the values of the first and second pressures P1 and P2, respectively, are displayed. Windows 79 and 80 are provided in the visual display screen 56 in which the values of the computed areas A1 and A2, respectively, corresponding to the first and second pressures P1 and P2, respectively, are displayed.

With the value of the distensibility index of the lower oesophageal sphincter 3 computed, the surgeon or physician can then compare the computed value of the distensibility index with reference values of distensibility indices of lower oesophageal sphincters, which would include a value of the distensibility index for a healthy lower oesophageal sphincter and values of the distensibility indices of lower oesophageal sphincters in various stages of GERD and other diseases and conditions such as achalasia. From this comparison the surgeon or physician can then classify the subject as suffering from GERD or other conditions, and if the subject is suffering from GERD, the seriousness of the condition can also be determined from the comparison. Similarly, in the case of the condition achalasia, the seriousness of the condition can also be determined from the comparison. Additionally, the microprocessor 22 may be programmed to make the comparison, and produce a report on the subject, which would confirm if the subject is suffering from GERD or other conditions, and the seriousness of the condition.

In another embodiment of the invention method for determining the distensibility of a vessel wall, a lumen wall or a sphincter determines the distensibility of the vessel wall, the lumen wall or the sphincter as a function of the slope m of the line y=mx+c. In this embodiment of the invention the slope m of the line y=mx+c is determined in the same manner as the slope m of the line y=mx+c is described as being determined with reference to blocks 65 to 74 of FIG. 6. In this case the distensibility is displayed on the screen 56 of the visual display unit 55 in an appropriate window (not shown) as the slope m of the line y=mx+c. Once the distensibility of the vessel wall, the lumen wall or the sphincter has been computed as the slope m of the line y=mx+c, the slope m is then compared with reference slopes of corresponding healthy and diseased vessel walls, lumen walls and sphincters, as the case may be, of different degrees of seriousness of the relevant disease or condition in order to determine the state of the vessel wall, the lumen wall or the sphincter under investigation. This comparison may be made manually or the microprocessor 22 may be programmed to make the comparison and produce a report on the state of the vessel wall, the lumen wall or the sphincter under investigation.

While the slope of the lines of graphs A and B of the line y=mx+c of the sphincters which are illustrated in FIG. 8 are substantially similar, in certain cases, the slopes of the line y=mx+c representative of lower oesophageal sphincters of different degrees of disease will not always be similar over the portion of the relationship of transverse cross-sectional area to pressure where the relationship is linear, and in such cases, the distensibility of a lower oesophageal sphincter may also be determined as either a function of the slope or of the slope of the line y=mx+c over the portion in which the relationship between transverse cross-sectional area and pressure of the lower oesophageal sphincter is linear.

Referring now to FIG. 9 a method according to another embodiment of the invention for determining the distensibility of a lower oesophageal sphincter will now be described. In this embodiment of the invention the distensibility of the sphincter is determined as the value of the transverse cross-sectional area of the sphincter when the balloon 12 acting on the sphincter is inflated to a known pressure, namely, a first pressure. The first pressure lies within the linear portion of the relationship of the transverse cross-sectional area of the sphincter and the pressure of the inflating medium in the balloon 12. In this embodiment of the invention the balloon 12 is inflated to the first pressure, which may be the same for all types of lower oesophageal sphincters, and in this embodiment of the invention is 15 mm of mercury, although in seriously diseased sphincters, the first pressure may be selected to be higher or lower than 15 mm of mercury as appropriate. The transverse cross-sectional area of the necked portion 62 of the balloon 12 which corresponds to the transverse cross-sectional area of the sphincter 3 is read from the sensing electrode 18 adjacent the necked portion 62 of the balloon 12 when the pressure of the inflating medium in the balloon 12 is at the first pressure of 15 mm of mercury. The transverse cross-sectional area of the necked portion 62 of the balloon 12 is computed from the signal read from the sensing electrode 18 adjacent the necked portion 62.

In this embodiment of the invention the microprocessor 22 is programmed to display a grid with values of transverse cross-sectional area of a lower oesophageal sphincter indicated on the vertical Y-axis and values of pressure of the inflating medium in a balloon indicated on the horizontal X-axis. Five areas are identified on the grid, namely, a first area H, a second area J, a third area K, a fourth area L and a fifth area P. The first area H is representative of a normal area, in which the distensibility value, namely, the value of the transverse cross-sectional area of the sphincter should fall if the lower oesophageal sphincter is a healthy sphincter when the pressure of the inflating medium in the balloon 12 is of a pressure within the range where the relationship between the transverse cross-sectional area of the sphincter and the pressure of the inflating medium in the balloon is a linear relationship. The second area J is an area in which the distensibility value of the sphincter would fall if the sphincter is a seriously diseased GERD sphincter. The third area K is representative of an area in which the distensibility value of the sphincter would fall if the sphincter is in the early stages of GERD. The fourth area L is an area in which the distensibility value of the sphincter would fall if the sphincter is seriously diseased with achalasia, in other words, seriously tightened, and the fifth area P is an area in which the distensibility value of the sphincter would fall if the sphincter is in the early stages of achalasia. However, in all cases it should be noted that the distensibility value of the lower oesophageal sphincter, which in this case is determined as the transverse cross-sectional area of the lower oesophageal sphincter when the balloon 12 has been inflated to the first pressure, must be determined where the relationship between the transverse cross-sectional area of the lower oesophageal sphincter and the pressure of the inflating medium in the balloon 12 is a linear relationship.

In FIG. 9 the distensibility value Q is displayed in the first area H, thus indicating a normal lower oesophageal sphincter.

While the method according to this embodiment of the invention which has been described with reference to FIG. 9 has been described for determining the distensibility of a lower oesophageal sphincter, this method may be used for determining the distensibility of any sphincter, and may also be used for determining the distensibility of a vessel wall or a lumen wall.

In a method according to a further embodiment of the invention, the distensibility of a vessel wall, a lumen wall or a sphincter is determined as being the pressure of the inflating medium in the balloon 12 when the balloon 12 has been inflated to a pressure at which the relationship between the transverse cross-sectional area of the vessel wall, lumen wall or sphincter and the pressure of the inflating medium in the balloon transitions from being linear to being non-linear. In other words, the distensibility is determined in this embodiment of the invention as the pressure of the inflating medium in the balloon 12 at the points R and S of the graphs A and B, respectively, of FIG. 8.

In this embodiment of the invention where the distensibility of a sphincter is being determined, the balloon 12 is progressively inflated, and during inflating of the balloon the signals from the sensing electrode 18 adjacent the necked portion 62 of the balloon 12 are continuously monitored in order to determine when the relationship between the transverse cross-sectional area of the sphincter and the pressure of the inflating medium in the balloon 12 transitions from the linear relationship to the non-linear relationship. Once the transition point has been determined, the distensibility of the sphincter is then determined as the pressure of the inflating medium in the balloon at the point at which the relationship between the transverse cross-sectional area of the sphincter and the pressure of the inflating medium in the balloon transitioned from being a linear relationship to a non-linear relationship.

In this embodiment of the invention, the distensibility may also be determined as the transverse cross-sectional area of the sphincter at the point at which the relationship between the transverse cross-sectional area of the sphincter and the pressure of the inflating medium in the balloon transitions from being a linear relationship to a non-linear relationship. Indeed, the distensibility may also be determined as the ratio of the transverse cross-sectional area of the sphincter to the pressure of the inflating medium in the balloon at the point at which the relationship between the transverse cross-sectional area of the sphincter and the pressure of the inflating medium in the balloon transitions from being a linear relationship to a non-linear relationship. Needless to say, the method according to this embodiment of the invention may be used for determining the distensibility of any sphincter, or the vessel wall or lumen wall of any vessel or lumen.

While the apparatus has been described for determining the distensibility index and the distensibility of a lower oesophageal sphincter, the apparatus 1 may be used for determining the distensibility index or the distensibility of any other sphincter. It is also envisaged that the apparatus 1 may be used for determining the distensibility index or the distensibility of a wall of a vessel or a lumen, and in which case, it is envisaged that the minimum value of the transverse cross-sectional area of the balloon 12 which would correspond to the minimum transverse cross-sectional area of the vessel or lumen would be computed as the areas A1 and/or A2 of the vessel or lumen which correspond with the respective first and second pressures.

It is also envisaged that the linear portion of the relationship between the transverse cross-sectional area of the sphincter and the pressure of the inflating medium in the balloon may be determined by progressively inflating the balloon and continuously computing values of the transverse cross-sectional area of the balloon adjacent the necked portion thereof corresponding to the transverse cross-sectional area of the sphincter corresponding to values of the pressure of the inflating medium in the balloon as the pressure of the inflating medium in the balloon is increased. A plot of the values of the transverse cross-sectional area of the sphincter against the corresponding pressures of the inflating medium in the balloon would be prepared and the first derivative of the plot would be computed for determining the portion of the plot of the values of the transverse cross-sectional area of the sphincter against the pressure of the inflating medium in the balloon over which the relationship between the values of the transverse cross-sectional area of the sphincter and the pressure of the inflating medium in the balloon is linear. The microprocessor would be programmed to determine the values of the first and second pressures or the first pressure, as the case may be, so that the first or the first and second pressures are within the linear portion of the plot of the values of the transverse cross-sectional area of the sphincter against the pressure of the inflating medium in the balloon.

Alternatively, in cases where the balloon is located in a sphincter and the microprocessor is programmed to take a number of readings of transverse cross-sectional area of the balloon at a plurality of pressures of the inflating medium within the balloon, the microprocessor could be programmed to produce an equation of a line resulting from the transverse cross-sectional/pressure readings, and to obtain the first derivative of the line to determine the portion of the line of constant slope. The equation of the portion of that line of constant slope, namely, y=mx+c would be derived, and the value of c would be obtained as the distensibility index of the sphincter. An advantage of obtaining a plurality of values of transverse cross-sectional area corresponding to a plurality of pressures is that it would provide a more accurate reading of the value c, and additionally, the microprocessor could be programmed to immediately identify the pressure at which the relationship between transverse cross-sectional area and pressure becomes non-linear, and at that stage, further increase in the pressure of the inflating medium within the balloon would cease. This would have the added advantage of avoiding the sphincter being subjected to excessive pressures. Indeed, it is envisaged that the pressures to which the balloon would be inflated may be predefined pressures, which would be programmed into the microprocessor.

It is also envisaged that the microprocessor could be programmed that on determining that the balloon has been inflated to a stage where it defines the sphincter without distending the sphincter, the microprocessor would increment the pressure in incremental steps from that pressure until the slope of a line representative of the relationship between the transverse cross-sectional area and pressure became non-linear. The steps in incremental pressures could be predefined, or the microprocessor could be programmed to set the increments at appropriate values based on the pressure of the inflating medium within the balloon when the balloon is inflated to the stage where it defines the sphincter without distending the sphincter.

It is also envisaged that instead of inflating the balloon to a first pressure or to first and second pressures, the balloon could be inflated to a first transverse cross-sectional area or first and second transverse cross-sectional areas adjacent the location where the balloon 12 is of minimum transverse cross-sectional area, and in which case, the corresponding pressures would be determined when the portion of the balloon where the transverse cross-sectional area is minimum had been inflated to the first and second transverse cross-sectional area.

While the measuring means of the balloon catheter of the apparatus according to the invention has been described as comprising stimulating and sensing electrodes, any other suitable measuring means for measuring the transverse cross-sectional area of the balloon adjacent a sphincter, or adjacent the vessel or lumen, the distensibility of which is to be determined may be provided. Indeed, in certain cases, it is envisaged that the means for measuring the transverse cross-sectional area of the balloon will monitor the volume of liquid inflating medium being pumped into the balloon, and the transverse cross-sectional area of the balloon will be determined from the total volume of inflating medium in the balloon.

While a particular type of pressure sensing means has been described, any suitable pressure sensing means may be provided, and while the pressure sensing means has been described as being located within the hollow interior region of the balloon, while this is advantageous, it is not essential.

While the distensibility index has been described as being the value c of the equation of the line y=mx+c, the distensibility index could be determined as the point of intersection of the X-axis by the line y=mx+c representative of the transverse cross-sectional area/pressure relationship of the sphincter 3 with the pressure of the inflating medium in the balloon, in other words, the pressure axis.

While the distensibility index of the sphincter has been described as being either the point on the X-axis or the Y-axis which is intersected by the line y=mx+c, the distensibility index could be determined as being a shift either upwardly or leftwardly of the equation of the line y=mx+c representative of the sphincter under test from the equation of a line y=mx+c representative of a healthy sphincter. The shift could be the vertical or horizontal distance, which would in effect be the same as the difference in the two values of c of the respective lines y=mx+c of the healthy sphincter and the sphincter under test or the distance between the points of intersection on the X-axis of the respective lines y=mx+c, or it could be a perpendicular distance between the two lines y=mx+c representative of the respective healthy sphincter and the sphincter under test.

While the apparatus has been described as comprising a pump for pumping the inflating medium into and out of the balloon, any other suitable inflating means may be provided. Indeed, it is envisaged in certain cases that the inflating means may be provided by a manually operated syringe, and in other cases, the syringe may be adapted to be mechanically operated, and in which case, the syringe would be operated under the control of the control circuit.

The invention claimed is:

1. A method for determining the distensibility of one of a vessel wall, a lumen wall and a sphincter, the method comprising:
    providing a balloon catheter comprising an elongated catheter extending between a proximal end and a distal end, and an inflatable element defining a hollow interior region when inflated located on the catheter, the inflatable element being adapted for locating in the one of the vessel, the lumen and the sphincter,
    locating the inflatable element of the balloon catheter in the one of the vessel, the lumen and the sphincter,
    inflating the inflatable element to a first pressure sufficient to distend the one of the vessel wall, the lumen wall and the sphincter,
    determining a first transverse cross-sectional area adjacent a portion of the one of the vessel wall, the lumen wall and the sphincter, at which the distensibility is to be determined when the inflatable element is inflated to the first pressure,
    inflating the inflatable element to a second pressure sufficient to distend the one of the vessel wall, the lumen wall and the sphincter,
    determining a second transverse cross-sectional area adjacent the portion of the one of the vessel wall, the lumen wall and the sphincter, at which the distensibility is to be determined when the inflatable element is inflated to the second pressure sufficient to distend the one of the vessel wall, the lumen wall and the sphincter,
    the values of the first and second pressures being different and being values at which the relationship between the transverse cross-sectional area of the inflatable element adjacent the portion of the one of the vessel wall, the lumen wall and the sphincter, at which the distensibility is to be determined and the pressure of an inflating medium in the inflatable element is a linear relationship,
    determining a linear equation of a line containing the values of the first and second transverse cross-sectional areas of the inflatable element adjacent the portion of the one of the vessel wall, the lumen wall and the sphincter, at which the distensibility is to be determined and the values of the first and second pressures of the inflating medium in the inflatable element corresponding to the first and second values of the transverse cross-sectional area thereof, the line being a plot of the values of the transverse cross-sectional area of the inflatable element adjacent the portion of the one of the vessel wall, the lumen wall and the sphincter, at which the distensibility is to be determined against the values of the corresponding pressure of the inflating medium in the inflatable element, and
    determining the distensibility of the one of the vessel wall, the lumen wall and the sphincter as a distensibility index, the distensibility index being the value of a point of intersection of the axis on which one of the transverse cross-sectional area and the pressure is plotted by the line, the equation of which contains the values of the first and second transverse cross-sectional areas of the inflatable element and the corresponding values of the first and second pressures of the inflating medium in the inflatable element.

2. A method as claimed in claim 1 in which the inflatable element is inflated to the first pressure prior to being inflated to the second pressure, the first pressure and the first transverse cross-sectional area being less than the second pressure and the second transverse cross-sectional area, respectively.

3. A method as claimed in claim 1 in which the value of one of the first and second transverse cross-sectional areas of the inflatable element adjacent the portion of the one of the vessel wall, the lumen wall and the sphincter, at which the distensibility is to be determined and the value of one of the first and second pressures of the inflating medium in the inflatable element are of values at which the relationship between the transverse cross-sectional area of the inflatable element and the pressure of the inflating medium in the inflatable element transitions from being a substantially linear relationship to a substantially non-linear relationship.

4. A method as claimed in claim 1 in which the inflatable element is provided as an elongated inflatable element extending between a proximal end and a distal end and is adapted for locating in a sphincter with the sphincter located intermediate the proximal end and the distal end thereof for determining the distensibility of the sphincter, so that when the inflatable element is inflated, the sphincter shapes the inflatable element to define a portion of minimum transverse cross-sectional area adjacent the sphincter.

5. A method as claimed in claim 4 in which the inflatable element is located in the sphincter so that the sphincter is located substantially mid-way between the proximal end and the distal end of the inflatable element.

6. A method for determining the distensibility of one of a vessel wall, a lumen wall and a sphincter, the method comprising:
    providing a balloon catheter comprising an elongated catheter extending between a proximal end and a distal end, and an inflatable element defining a hollow interior region when inflated located on the catheter, the inflatable element being adapted for locating in the one of the vessel, the lumen and the sphincter, locating the inflatable element of the balloon catheter in the one of the vessel, the lumen and the sphincter, inflating the inflatable element to a first transverse cross-sectional area adjacent a portion of the one of the vessel wall, the lumen wall and the sphincter, at which the distensibility is to be determined, sufficient to distend the one of the vessel wall, the lumen wall and the sphincter, determining a first pressure adjacent the portion of the one of the vessel wall, the lumen wall and the sphincter, at which the distensibility is to be determined when the inflatable element is inflated to the first transverse cross-sectional area, inflating the inflatable element to a second transverse cross-sectional area adjacent a portion of the one of the vessel wall, the lumen wall and the sphincter, at which the distensibility is to be determined, sufficient to distend the one of the vessel wall, the lumen wall and the sphincter, determining the second pressure when the inflatable element is inflated to the second transverse cross-sectional area, the values of the first and second pressures and the first and second transverse cross-sectional areas being different and being values at which the relationship between the transverse cross-sectional area of the inflatable element adjacent the portion of the one of the vessel wall, the lumen wall and the sphincter, at which the distensibility is to be determined and the pressure of an inflating medium in the inflatable element is a linear relationship, determining a linear equation of a line containing the values of the first and second transverse cross-sectional areas of the inflatable element adjacent the portion of the one of the vessel wall, the lumen wall and the sphincter, at which the distensibility is to be determined and the values of the first and second pressures of the inflating medium in the inflatable element corresponding to the first and second values of the transverse cross-sectional area thereof, the line being a plot of the values of the transverse cross-sectional area of the inflatable element adjacent the portion of the one of the vessel wall, the lumen wall and the sphincter, at which the distensibility is to be determined against the values of the corresponding pressure of the inflating medium in the inflatable element, and determining the distensibility of the one of the vessel wall, the lumen wall and the sphincter as a distensibility index, the distensibility index being the value of a point of intersection of the axis on which one of the transverse cross-sectional area and the pressure is plotted by the line, the equation of which contains the values of the first and second transverse cross-sectional areas of the inflatable element and the corresponding values of the first and second pressures of the inflating medium in the inflatable element.

7. A method as claimed in claim 6 in which the inflatable element is inflated to the first transverse cross-sectional area prior to being inflated to the second transverse cross-sectional area, the first pressure and the first transverse cross-sectional area being less than the second pressure and the second transverse cross-sectional area, respectively.

8. A method as claimed in claim 6 in which the value of one of the first and second transverse cross-sectional areas of the inflatable element adjacent the portion of the one of the vessel wall, the lumen wall and the sphincter, at which the distensibility is to be determined and the value of one of the first and second pressures of the inflating medium in the inflatable element are of values at which the relationship between the transverse cross-sectional area of the inflatable element and the pressure of the inflating medium in the inflatable element transitions from being a substantially linear relationship to a substantially non-linear relationship.

9. A method as claimed in claim 6 in which the inflatable element is provided as an elongated inflatable element extending between a proximal end and a distal end and is adapted for locating in a sphincter with the sphincter located intermediate the proximal end and the distal end thereof for determining the distensibility of the sphincter, so that when the inflatable element is inflated, the sphincter shapes the inflatable element to define a portion of minimum transverse cross-sectional area adjacent the sphincter.

10. A method as claimed in claim 9 in which the inflatable element is located in the sphincter so that the sphincter is located substantially mid-way between the proximal end and the distal end of the inflatable element.

* * * * *